United States Patent [19]

Damadian

[11] Patent Number: 5,515,863
[45] Date of Patent: May 14, 1996

[54] GASTROINTESTINAL MAGNETIC RESONANCE IMAGING

[75] Inventor: Raymond V. Damadian, Woodbury, N.Y.

[73] Assignee: Fonar Corporation, Melville, N.Y.

[21] Appl. No.: 178,741

[22] Filed: Jan. 7, 1994

[51] Int. Cl.⁶ ................................................ A61B 5/055
[52] U.S. Cl. ................................................ 128/653.4
[58] Field of Search ........................ 128/653.2, 653.4, 128/653.5

[56]     References Cited

U.S. PATENT DOCUMENTS 5,070,213  12/1991  Huang et al. .................... 128/653.4
5,277,896   1/1994  Balkus, Jr. ....................... 128/653.4
5,303,705   4/1994  Nenov ............................. 128/653.2
5,305,749   4/1994  Li et al. .......................... 128/653.2
5,320,826   6/1994  Unger ............................. 128/653.4
5,380,514   1/1995  Waigh et al. .................... 128/653.4

*Primary Examiner*—Ruth S. Smith
*Attorney, Agent, or Firm*—Brooks Haidt Haffner & Delahunty

[57]     ABSTRACT

Gastrointestinal MRI using an ingested contrast material. Provision is made for tracking the passage of a bolus of the contrast material through the gastrointestinal tract.

27 Claims, 5 Drawing Sheets

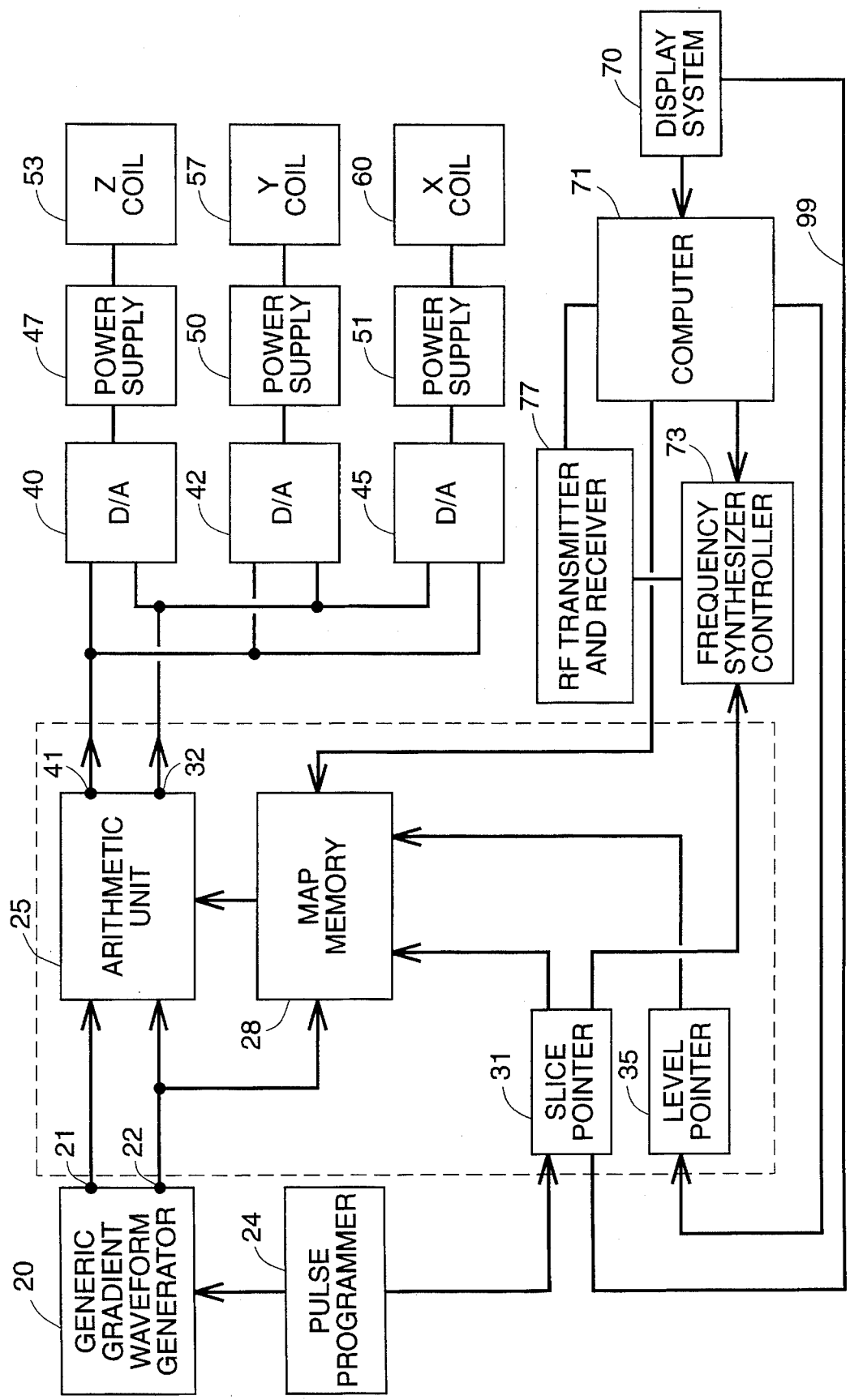

GASTROINTESTINAL MAGNETIC RESONANCE IMAGING

BACKGROUND OF THE INVENTION

The present invention relates to improved apparatus for and methods of magnetic resonance imaging, and more particularly to gastrointestinal magnetic resonance imaging.

Magnetic resonance imaging (MRI) has enjoyed enormous success, in part because of the excellent contrast in tissue images which it inherently produces. In addition, MRI does not expose the patient to ionizing radiation such as x-rays.

One application of x-rays still in widespread use is in the area of gastrointestinal imaging. The gastrointestinal (GI) tract is imaged by having the patient drink a suitable contrast material, such as a barium-containing compound, and acquiring x-ray images of the region of the gastrointestinal tract in which the contrast material is located. For example, esophageal imaging is carried out by having a patient swallow a barium-containing liquid, and by imaging the patient's esophagus while the liquid traverses the esophagus. Similar procedures are used for imaging other regions of the GI tract.

It would be highly desirable to obtain sufficient image data during the course of a GI study in order to create cine displays of the GI tract as it functions, e.g. during swallowing. X-ray exposure limits, however, create practical limitations on the extent to which data for GI cines can be acquired.

Accordingly, it is an object of the invention to provide a practical method for MRI studies of the GI tract.

Another object of the invention is to provide an MRI system which has features to facilitate the acquisition and display of cine MRI studies of the GI tract.

Another object of the invention is to provide a method for acquiring GI images by MRI and which can be displayed in a cine format to show GI tract anatomical function as well as structure.

It is still another object of the invention to provide improved MRI imaging techniques for imaging complex structures which do not lie substantially in a single image slice.

SUMMARY OF THE INVENTION

According to the invention magnetic resonance data is acquired by positioning a patient for magnetic resonance imaging of the GI tract. The patient ingests contrast material which exhibits high contrast in magnetic resonance images, and a sequence of magnetic resonance data sets is acquired. Each data set corresponds to a magnetic resonance image of the patient's GI tract during the course of ingestion of the contrast material or passage of the contrast material through the GI tract. As an additional step of the method, the acquired data is displayed as a cine sequence of images in order to show swallowing and motion of the bolus of contrast material through the GI tract, as well as showing the GI tract structure.

In another preferred embodiment of the invention a patient ingests contrast material which exhibits high contrast in magnetic resonance images, and a sufficient length of time elapses to allow the ingested material to reach a particular portion of the patient's GI tract. The patient is positioned for magnetic resonance imaging of the GI tract portion containing the contrast material, and a sequence of magnetic resonance data sets, each corresponding to a magnetic resonance image of the contrast material within the patient's GI tract, during the course of passage of the material, is acquired. As an additional step of the method, the acquired data is displayed as a cine sequence of images in order to show the function as well as the structure of the GI tract.

As the bolus of contrast material travels through the GI tract it changes position relative to the patient axis over its entire path of travel. According to one preferred embodiment of the invention, bolus tracking during data acquisition is used. This is achieved by acquiring a sequence of magnetic resonance data sets each corresponding to an image slice of the contrast material within the patient's GI tract. Data sets corresponding to thick image slices along a pair of orthogonal orientations are acquired. As an example, paired data sets are acquired sequentially, and the position of the contrast material within the image represented by a data set is determined before the acquisition of a successive data set. Based on the change in position over time of the contrast material from two successive sets of paired slices, the position of the contrast material for a future data set at a predetermined time is estimated. The future data set is acquired with the image slices positioned at the estimated new position of the material. The process is repeated as often as necessary to obtain a complete visualization of the regions of the GI tract of interest.

In an alternative embodiment the contrast material within the GI tract is imaged by acquiring data sets by thick slice magnetic resonance acquisition. The acquisition of thick slice image data can be carried out at the Larmor frequency of the patient, in which case it may be preceded by acquisition of image data for the patient's GI tract prior to the contrast material reaching that anatomy. The data can then be subtracted to produce image data for just the contrast material. Alternatively, the acquisition of thick slice image data can be carried out at a Larmor frequency of the contrast material that is different than that of the patient so that the acquired image data will contain image information for only the contrast material. This embodiment requires that the contrast material have a suitable Larmor frequency.

BRIEF DESCRIPTION OF THE DRAWINGS

FIG. 4 is a block diagram of an apparatus according to the invention for carrying out disclosed methods according to the invention.

DETAILED DESCRIPTION OF THE PREFERRED EMBODIMENT

As used herein, "contrast material" shall mean a material which exhibits a high contrast in a magnetic resonance image with respect to the body tissues surrounding it. Contrast materials include materials which emit a magnetic resonance signal and exhibit a contrast different than surrounding tissues and materials which do not emit a magnetic resonance signal. Contrast materials are to be distinguished from contrast agents used in MRI which are used to alter tissue relaxation time and thereby alter tissue image contrast within a magnetic resonance image. We define the term contrast materials to be a more general term which may include contrast agents as herein defined but may also include materials that have their own resonance and therefore their own visibility in a magnetic resonance image.

Figure 1A:
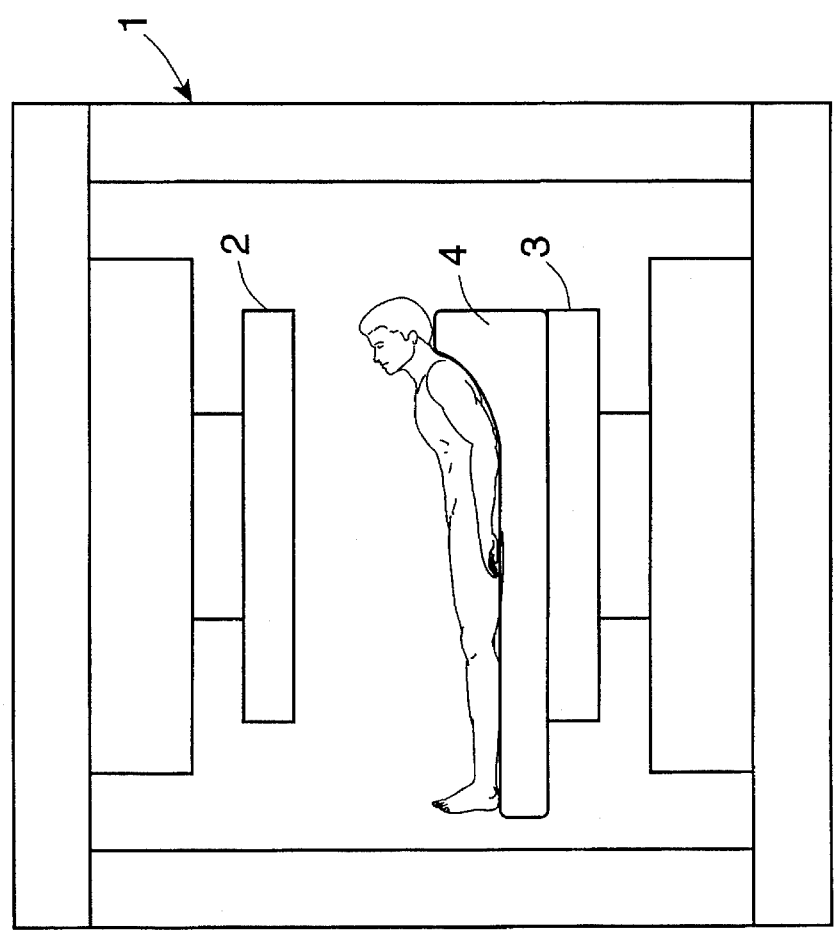
FIG. 1A shows a patient positioned for gastrointestinal tract imaging by the method according to the invention.

According to the invention magnetic resonance image data is acquired from the GI tract by positioning a patient for magnetic resonance imaging of that region. FIG. 1A shows a patient positioned in a magnet 1 between the magnet poles 2 and 3 in a reclining position. A cushion 4 elevates the patient's head and neck so that a contrast material used in the data acquisition can be comfortably swallowed with assistance from gravity by the patient. The cushion 4 also serves to stabilize the patient's abdomen to prevent unwanted movement during scanning, and, if desired, an abdominal belt can be added to the cushion to help immobilize the patient's abdomen.

Figure 1B:
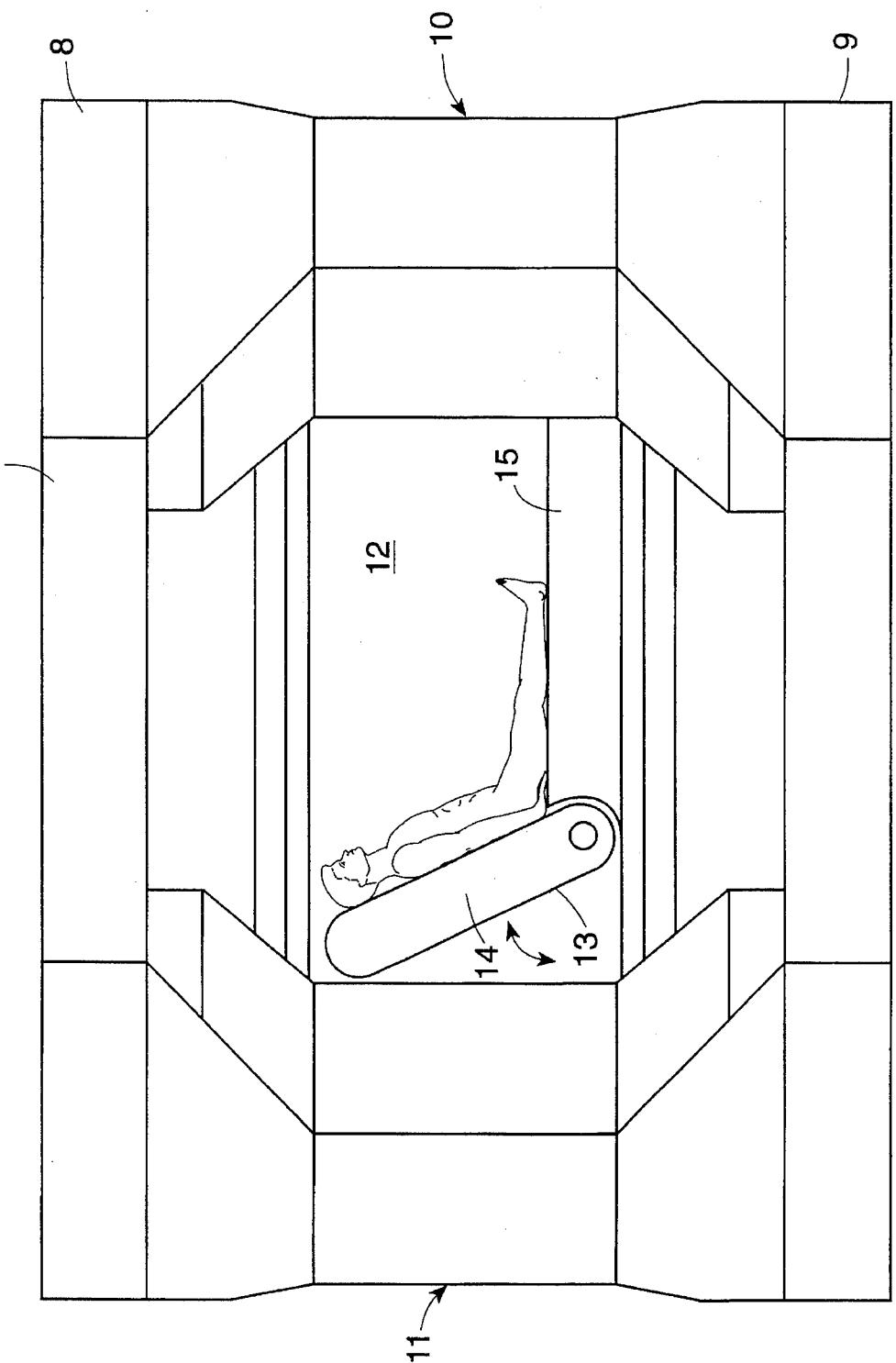
FIG. 1B, shows a patient positioned for gastrointestinal tract imaging with the use of an adjustable patient support in an open access magnet.

FIG. 1B is a side view of another magnet 7 in which a patient is shown with his upper torso inclined relative to his lower torso. A ferromagnetic yoke of the magnet 7 is comprised of upper and lower plates 8 and 9 supported by ferromagnetic columns. Two of the columns 10 and 11 are in view in the drawing, and two other columns are hidden from view. The columns are configured to maximize access to the patient receiving space 12 of the magnet, and to this end the columns of the magnet yoke are dimensioned and configured to minimize obstruction to patient access to and egress from the patient receiving space 12. The magnet 7 is an example of open access magnets for magnetic resonance which are the subject of U.S. patent application Ser. No. 952,810 filed on Sep. 28, 1992, and U.S. patent application Ser. No. 993,072 filed on Dec. 18, 1992, and both commonly assigned to the assignee of the present application.

While in the space 12 the patient is supported on an adjustable patient support 13 having a portion 14 which is movable relative to a stationary portion 15. The patient rests with his head and upper torso against the patient support portion 14 which can pivot to change its inclination as indicated by the double headed arrow. With the patient resting in the position shown his upper torso is positioned relative to his lower torso so that gravity will assist the swallowing of contrast material. The use of adjustable patient positioning and an elevated patient upper torso allows that patient to swallow contrast material comfortably, avoids patient gagging and reduces motion artifacts. In addition, the use of an open access magnet provides improved access for patient positioning and adjusting upper torso elevation, for permitting a greater range of upper torso inclination than in a conventional magnet and for administering contrast material while the patient is in position within the space 12.

While being positioned within the magnet the patient ingests a contrast material which exhibits high contrast in magnetic resonance images. For some parts of the GI tract such as the esophagus, it is advantageous to acquire contrast material image data at the same Larmor frequency as the patient. Consequently, a hydrogen-rich material, for example, mineral oil, can be used as an effective contrast material for GI tract imaging. Alternatively, a solid or semi-solid contrast material can be used.

Because the human esophagus lies generally within a plane, two dimensional imaging can be used for the esophageal portion of the GI tract. Likewise, two dimensional image data acquisition in a different plane can be used for the stomach portion of the GI tract. As an alternative, data for the different parts of the GI tract can be acquired by three dimensional image data acquisition.

A sequence of data sets is acquired during the course of ingestion of the contrast material by the patient. Each of the data sets corresponds to a magnetic resonance image of the patient's GI tract at a different time during the course of the ingestion of the contrast material. A series of MRI images wherein the contrast material is in different positions can be obtained and reduced to a motion picture of the peristaltic action of the GI tract that illustrates the functioning of the GI tract during ingestion of the contrast material.

A contrast material which emits no magnetic resonance signal can be used. In this case, the image contrast will arise from the image of the esophagus and the region where the contrast material is within the esophagus and where there is no image. An advancing bolus of a zero signal material will optimize the contrast between the intestinal lining and intestinal cavity and optimize the contrast of the moving bolus of material. The use of the high contrast material that emits a magnetic resonance signal facilitates rapid acquisition of the data sets. Moreover, if the contrast material emits a strong magnetic resonance signal itself, the image of the contrast material will exhibit a high signal-to-noise ratio even with a short scan time. As a result, each data set can be acquired in less time than if image contrast were to be determined solely by the tissues being imaged.

Figure 2:
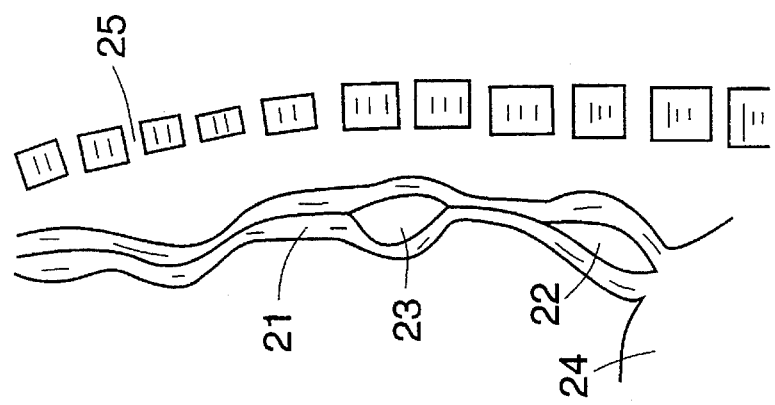
FIG. 2 depicts an image of the esophageal portion of the gastrointestinal tract acquired by the method according to the invention.

Normally, the esophagus appears in a collapsed condition in magnetic resonance images. During swallowing, the esophagus expands as ingested material travels through it. When the ingested material has a high inherent MRI contrast, magnetic resonance images will prominently show the esophagus in its expanded condition and show the function of the esophagus during swallowing. FIG. 2 is a sketch of the esophageal region 21 of the GI tract as it would appear in a magnetic resonance image with the esophagus distended by a bolus 22 of contrast material and a second bolus 23 passing through it and exhibiting a bright appearance in the image. Thus, the configuration that the esophagus takes during swallowing is readily apparent in the magnetic resonance image and permits direct observation of esophageal function. In order to localize the imaged anatomy a portion of the stomach 24 and spinal column 25 also appear in the image.

The dynamic behavior of the esophagus during swallowing can be readily seen by displaying the sequence of magnetic resonance images in a cine display. The images derived from the sequence of data sets are displayed sequentially and at a sufficient rate to show the motion of the esophagus during the course of swallowing so that the observing physician can see how the esophagus changes configuration in the course of swallowing. There is no physiological limitation on the number of images acquired resulting from exposure limits to ionizing radiation such as there would be with x-rays. The limitations are technological in nature and are related to how rapidly the MRI system being used can acquire the image data.

The methods according to the present invention can be practiced using conventional spin echo techniques. In order to reduce motion artifacts in the images resulting from swallowing or peristaltic motion gradient echo methods, fast spin echo acquisition techniques, echo planar techniques or pulse sequences with inherent motion compensation can be used.

Everything that has been said with regard to the esophageal portion of the GI tract applies as well to the stomach portion of the GI tract. A suitable planar image slice orientation is selected and a contrast material having a high inherent contrast is introduced into that portion of the GI tract to be imaged. A suitable number of image data sets is acquired, and the images are displayed for viewing.

Because the intestinal portion of the GI tract is not a generally planar structure, imaging of it requires a somewhat different method than that previously discussed. If a single imaging plane is selected, the bolus of contrast material will move into and out of that single imaging plane as it traverses the length of the intestinal tract. Accordingly, in order to maintain the bolus of contrast material within the image plane, the image plane must be thick or its position must be changed during the course of data acquisition.

Magnetic resonance imaging of the intestinal portion of the GI tract is carried out according to the present invention by having the patient ingest contrast material which exhibits high contrast in magnetic resonance images. A sufficient length of time is then waited to allow the ingested contrast material to reach the patient's intestinal tract. Next, the patient is positioned within a magnetic resonance imaging system for imaging of the patient's intestinal tract. A sequence of data sets are acquired wherein each corresponds to a magnetic resonance image of the contrast material within the patient's intestinal tract during the course of passage of the contrast material through the intestines.

In one preferred embodiment of the invention the acquired data sets represent adjacent image slices through the region of the GI tract which is of interest. The image data for the respective slices is then juxtaposed to create a three-dimensional representation of the portion of the GI tract which is of interest and the contrast material therein. If the contrast material emits a strong signal, i.e. if it exhibits a high signal to noise ratio in the image, then the aggregate of the acquired data sets can be used to display a three-dimensional representation of a selected portion of the GI tract and any contrast material within that portion of the GI tract. This three-dimensional representation can be displayed as a static image, or it can be rotated in the conventional fashion to allow the displayed portion of the GI tract and contrast material to be viewed from different directions.

Another preferred embodiment uses three-dimensional (3-D) data acquisition. According to this method, a volume larger than and fully containing the bolus of contrast material is imaged by 3-D data acquisition. At a later time, after the bolus has moved some distance within the GI tract, another 3-D data set is acquired which contains the displaced bolus of contrast material. The second and subsequent 3D data acquisition is always chosen so that its position and dimensions must contain the bolus somewhere in its 3D field of view for any reasonable and normal value of G.I. transit time which has been previously determined by MRI imaging. These steps are repeated until data is acquired for the entire path of the bolus through the portion of the GI tract which is of interest. The acquired data can then be displayed as static images, in a cine format, or as a composite image showing the bolus simultaneously at every position within the GI tract through which it passed. This data which was acquired by 3-D acquisition can be displayed in various visual formats. For example, a 3-D bolus image can be rotated to view it from various directions, or image reconstruction can be carried out so that selected two-dimensional slice planes are displayed for viewing.

In one preferred embodiment a sequence of pairs of data sets are acquired. Each data set corresponds to a magnetic resonance image of the patient's GI tract, and each pair of data sets corresponds to a pair of orthogonal image slices of the contrast material within the patient's intestines. The data sets are acquired successively, and the position of the contrast material within the image represented by a data set is determined before the acquisition of a next successive data set. After the contrast material position has been determined, from the known position of the slices in which the contrast material appears a second data set is taken, the new position of the contrast material is determined and the intestinal transit time of the material estimated. From the intestinal transit time estimated in this pair of data sets successive multi-slice data sets can be positioned with multi-slice ranges large enough to assure that the contrast material always falls within the range of the multi-slice set in successive data sets.

The image slice pair used may be a sagittal slice and a coronal slice, or a transaxial and coronal slice. Each slice of the orthogonal slice pair has a thickness greater than the largest dimension of the bolus of contrast material for which image data is being acquired. After a data set has been acquired the bolus position is compared by software with the position predicted from the previous data acquisition and the bolus position for the next data set is predicted.

An alternative preferred embodiment makes use of thick slice imaging. Thick slice imaging is achieved by conventional Fourier transform imaging, but without the slice select magnetic field gradient. The omission of a slice select gradient will cause the resulting image to be a projection of the entire thickness of the object being imaged. Thus, if thick slice imaging is carried out on the patient's intestinal tract region, but without a slice select gradient in the anterior-posterior dimension of the patient, the resulting magnetic resonance image is of the intestinal portion of the GI tract projected onto a single plane.

Thick slice imaging has the disadvantage that all of the patient anatomy along the anterior-posterior dimension appears in the image. The static tissues can be removed in the MRI with the following invention. The same drawback also exists in conventional radiographic techniques but can not be readily overcome in this modality because slice thickness is not easily altered in the x-ray methods. In this invention the static tissues can be removed (or greatly diminished) by acquiring a thick slice magnetic resonance image of the intestinal portion of the GI tract anatomy without contrast material present. Then image data for the images with the contrast material present and data for the images with the contrast material absent are subtracted. The difference data will be an image of the contrast material only within the intestinal portion of the GI tract in the thick slice with the image of the static patient anatomy suppressed or altogether absent. If this technique is carried out for two slice orientations, the bolus location can be determined exactly. For example, if thick slice coronal image data, with and without the bolus present, is acquired, and thick slice transaxial image data, with and without the bolus present, is also acquired, then the bolus image can be displayed properly positioned relative to the patient axis and with the static patient anatomy suppressed or absent from the displayed image.

Another alternative to bolus tracking is thick slice imaging at a Larmor frequency different than that of the patient's tissue. Conventionally, biological magnetic resonance imaging is carried out at the Larmor frequency of the hydrogen proton because of the abundance of hydrogen in tissue. If the contrast material is rich in hydrogen it will appear prominently on the magnetic resonance image, and data acquisition for the contrast material and the rest of the patient's anatomy can occur simultaneously. In the alternative embodiment of the invention, a contrast material is used which has a Larmor frequency different than that of hydrogen. Data is acquired at the Larmor frequency of the contrast material, and not at the frequency of hydrogen within the human body, so that the resulting magnetic resonance image will be a thick slice image of only the contrast material.

The contrast material used for this technique may be small particles of a material having a selected Larmor frequency different than that of hydrogen and encapsulated in biologically inert and non-digestible shells. The small composite particles can be suspended in a suitable fluid or mixed in with a solid or quasi-solid and ingested by the patient. The bolus containing these particles will then traverse the small intestine in a normal fashion and emit magnetic resonance signals to permit the acquisition of data sets corresponding to the desired thick slice images.

The image data acquired from the intestinal portion of the GI tract can be displayed in a cine format, if desired, to show the function of the intestinal tract just as in the case of the esophagus or stomach. Alternatively, the images can be viewed as static images in the conventional fashion.

FIGS. 3A–3L illustrate the imaging of a bolus 27 of contrast material as it passes through the small and large intestines of a patient. In the interest of clarity the small intestine is shown much shorter than its actual length, and in FIGS. 3A–3F the transverse colon portion of the large intestine is cut away to expose part of the underlying small intestine.

Figure 3A:
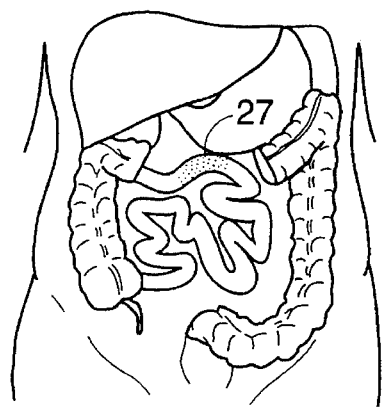
FIGS. 3A–3L depict images of the intestinal portion of the gastrointestinal tract acquired by the method according to the invention and showing a bolus of contrast material passing through it.
Figure 3B:
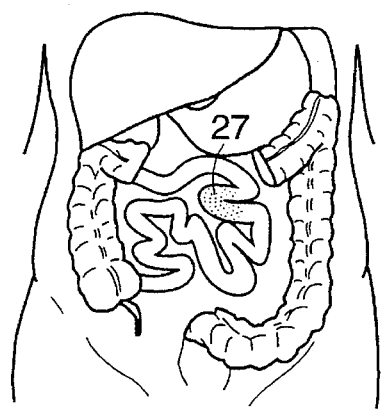
Figure 3C:
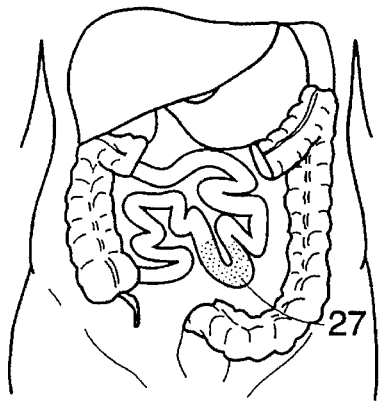
Figure 3D:
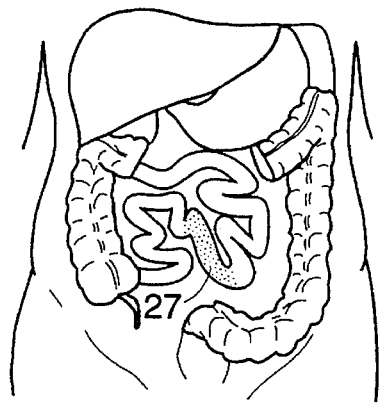
Figure 3E:
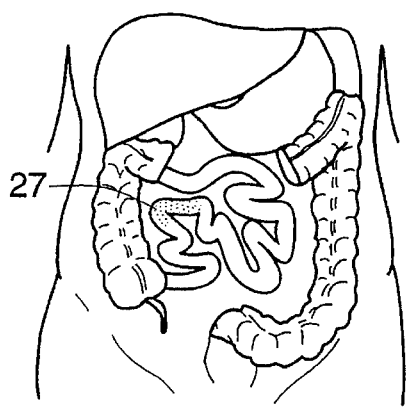
Figure 3F:
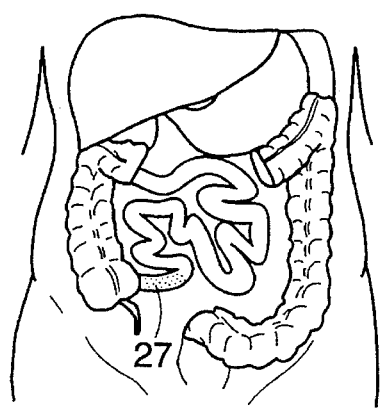

In FIG. 3A the contrast material 27 is high in the small intestine after having emerged from the stomach. With the elapse of time the contrast material 27 progresses through the small intestine in a direction away from the stomach and toward the ascending colon of the large intestine. This path of travel is depicted in FIGS. 3B–3F.

Figure 3G:
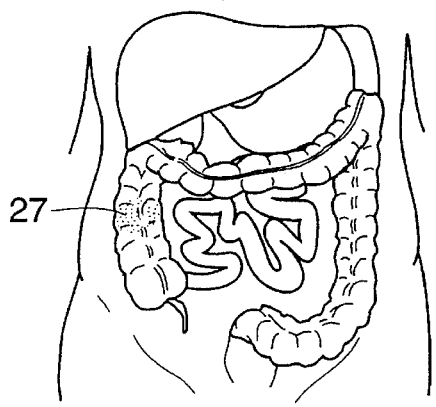
Figure 3H:
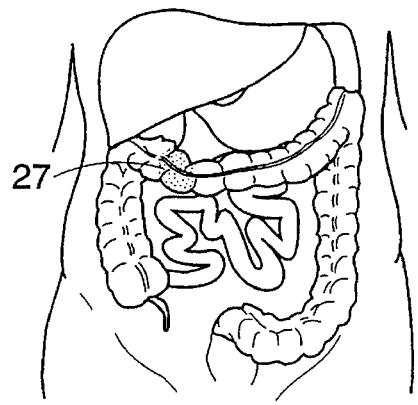
Figure 3I:
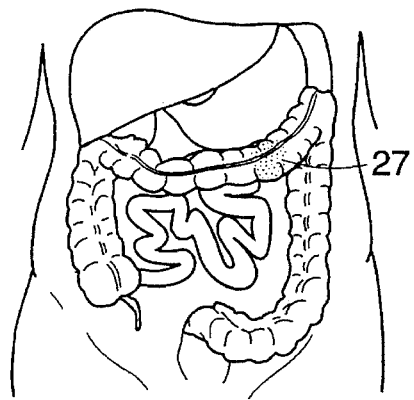
Figure 3J:
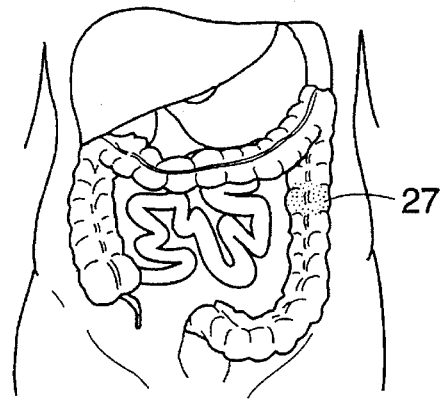
Figure 3K:
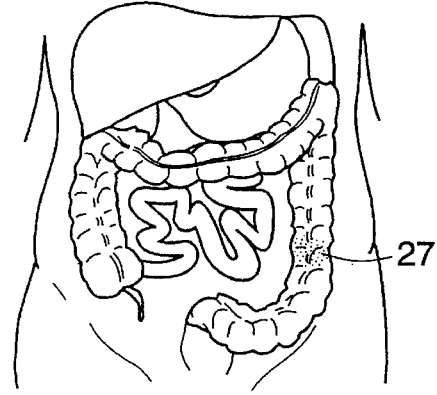
Figure 3L:
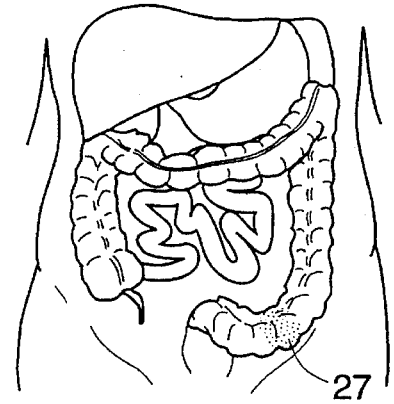

FIG. 3G shows the contrast material 27 after it has entered the ascending colon of the large intestine. The contrast material progresses through the large intestine in the same manner as through the small intestine; FIGS. 3H and 3I show the contrast material in the transverse colon, FIGS. 3J and 3K show the contrast material in the descending colon, and FIG. 3L depicts the contrast material in the sigmoid colon before passage into the rectum.

Bolus tracking can be carried out in the following manner. First, an initial scout scan is carried out in order to locate the position of the contrast material within the intestinal tract. Then the future position of the bolus at some later predetermined time is predicted. The future position prediction is obtained through the use of a predetermined nominal map of the intestinal tract, which may be a look-up table correlating transit time and bolus position within the intestinal tract. If the bolus position is known at some time, then a future position of the bolus can be estimated by looking up the later position in the look-up table that contains the normal and diseased range of transit times for a particular region of the intestine.

After the future position of the bolus is predicted the two orthogonal imaging slices are positioned at the predicted position. More particularly, the values and directions of the magnetic field gradients that will be used for slice selection and read out in the data acquisition process are determined according to the values of the predicted position that the bolus of contrast material will have at the time of data acquisition. Then when the predetermined time has elapsed data is acquired at the position previously predicted and for which the slice select and read out gradients were set with the stack of multi-slices positioned to assure capture of the imaging bolus within the multi-slice stack.

The acquired data set is Fourier transformed in the usual fashion and image data in the form of image pixel values is generated. The image data is tested to determine the bolus location, for example by a computer search to identify the high intensity pixel group which comprises the bolus of contrast material. The bolus position determined from the image data is compared with the previously predicted bolus position and the difference indicates whether the bolus actually traveled further than, or not as far as, the predicted position.

The sequence of steps just described is repeated, with the measured position of the bolus taken as the initial position, and a new predicted position for the bolus at some predetermined later time is generated from the nominal map of the intestinal tract and from the difference between the predicted and measured values of the bolus position determined in the previous step.

If we let the position $P(x,y,z,t)=P$ of the bolus be defined in some frame of reference and the position at particular times to be denoted $P_i=P(t_i)$, then the nominal map M of the intestinal tract can be conveniently represented as a set $M=((t_o, p_o), (t_1, P_1), \ldots (t_n, P_n))$. With this convention, the map M will predict a position change between times $t_{i-1}$ and $t_i$ of $$\Delta P_{i-1}=P_i-P_{i-1} \qquad (1)$$

and the predicted position at time $t_i$ will be given by $$P_i=P_{i-1}+\Delta P_{i-1} \qquad (2)$$

Moreover, if the actual measured position at time $t_i$ is represented by $P_{im}$ then the error in position between the predicted and measured position at time $t_i$ is given by $$eP_i=P_i-P_{im} \qquad (3)$$

Accordingly, the prediction of the bolus position can be improved by taking into account the error in prediction for the previous bolus position as follows:

$$P_i=P_{i-1}+\Delta P_{i-1}+eP_{i-1}. \qquad (4)$$

By using an image slice thickness greater than the measurement error $eP_i$, the bolus will always be within the image slices, and data acquisition can proceed through a sequence of acquisition times without having to perform a scout scan to locate the bolus of contrast material each time. In the bolus tracking mode data acquisition can be carried out automatically, after data acquisition has been initiated.

Although bolus tracking has been described with reference to an orthogonal slice-pair comprising two slices which are generally orthogonal to the principal patient axes, the invention is not so limited. For example, a preferred embodiment of the invention includes the use of a map M of the intestinal tract augmented with a preferred orientation for at least one of the image slices that will be used to acquire data at each map position. For example, the map M2 is a set of position-time pairs which also include information about the image slice orientation at each map position $P(x,y,z,t,\Theta)$ where $\Theta$ is the angle between one of the slices and a principal axis of the patient. Thus, the angular orientation of the image slices will be changed as the bolus of contrast material travels through the intestines and data is acquired at positions along the intestinal tract.

Provision must be made for changing image slice orientation. This can be achieved by adapting the apparatus and method disclosed in commonly assigned U.S. Pat. No. 4,871,966 for Apparatus And Method For Multiple Angle Oblique Magnetic Resonance Imaging. In the adapted system shown in FIG. 4, slice orientation is changed automatically according to the slice orientation parameter of the stored map of the intestines.

The block diagram shown in FIG. 4 is derived from FIG. 7 of the mentioned U. S. Pat. No. 4,871,966 but includes the subject matter specific to the present invention. The generic gradient waveform generator 20 is responsive to the pulse programmer 24 for generating a generic waveform at output terminal 21 and an axis select signal at output terminal 22. The generic waveform, when properly scaled and offset, will be the slice select gradient and read out gradient waveforms used for acquiring magnetic resonance image slice data. The generic waveform data from terminal 21 is applied to the arithmetic unit 25 where the numerical scaling and offset operations are performed.

The map memory 28 stores a table of value sets corresponding to the values $(x_i, y_i, z_i, t_i, \Theta_i)$ where $x_i, y_i, z_i$ are the spatial coordinates of the bolus at time $t_i$, and $\Theta_i$ is the orientation of a rotated frame of reference in which the image slices positions are specified. The gradient waveforms are computed according to the following equation:

$$SS(t_i) = C_{ss} (G(t) (\cos\Theta_i + \sin\Theta_i) + A(\cos\Theta_i - \sin\Theta_i)),$$

and, $$RO(t_i) = C_{ro}(G(t) (\sin\Theta_i - \cos\Theta_i) + A(\sin\Theta_i + \cos\Theta_i)),$$

where $SS(t_i)$ is the slice select gradient waveform used at the time $t_i$ of data acquisition, $RO(t_i)$ is the readout gradient waveform used at the time $t_i$ of data acquisition, $C_{ss}$ and $C_{ro}$ are constants of proportionality, $G(t)$ is the generic gradient waveform, $\Theta_i$ is the angle of rotation of a rotated frame of reference in which the image slice positions are specified, and amplitude A is an offset value.

A more detailed discussion of the foregoing equations is set forth in the cited U.S. Pat. No. 4,871,966.

The remainder of the circuit operates in the same manner as is described in the cited patent. The arithmetic unit 25 computes the gradient waveforms based on the information stored in the map memory 28, and the gradient waveform data is applied to the digital-to-analog (D/A) converters 40, 42, 45 where they are converted to analog signals. The analog waveforms are applied to control the power supplies 47, 50, 51 which in turn develop the signals for powering the gradient coils 53, 57 and 60 for the different spatial directions z, y and x, respectively. The frequency synthesizer 73 operates under computer control for applying an RF signal of the correct frequency to the transmitter and receiver 77. Phase encoding levels are set by the level pointer 35 under computer control, and slice selection is made by the slice pointer 31 under computer control. The computed slice position includes the slice position correction of eqn. 4 which is computed by the computer 71 to achieve bolus tracking, if that mode of operation is to be used.

The practicing of the present invention is independent of any particular type of magnetic resonance imaging system. In particular, it can be carried out on any convenient magnet configuration and is not limited to the types of magnets shown herein. Accordingly, the scope of the invention should be determined from the following claims.

I claim:

1. A method of imaging the dynamic behavior of the gastrointestinal tract of a patient comprising the following steps:

(a) positioning said patient within a magnetic resonance imaging apparatus;

(b) having said patient ingest a magnetic resonance image contrast material;

(c) determining an initial spatial position of said contrast material within the gastrointestinal tract of said patient and an initial slice orientation for at least one magnetic resonance image slice of a portion of said gastrointestinal tract containing said contrast material;

(d) acquiring said at least one image slice;

(e) calculating the spatial position of said contrast material within said gastrointestinal tract of said patient at a predetermined period of time after said acquiring said image slice;

(f) determining a slice orientation for at least one magnetic resonance image slice of another portion of said gastrointestinal tract containing said contrast material at said spatial position; and (g) repeating steps (d)–(f) a plurality of times, each repetition spaced apart for said predetermined period of time, to image the dynamic behavior of at least a portion of said gastrointestinal tract caused by the passage of said contrast material therethrough.

2. The method according to claim 1, wherein said steps (d)–(f) are repeated a multiplicity of times to create a cine of the dynamic behavior of at least a portion of said gastrointestinal tract of said patient caused by the passage of said contrast material therethrough.

3. The method according to claim 1, wherein said patient ingests said contrast material prior to being positioned within said magnetic resonance imaging apparatus.

4. The method according to claim 1, further comprising the step of waiting a period of time to allow contrast material in step (b) to reach a particular portion of said gastrointestinal tract prior to determining the position of said contrast material in step (c).

5. The method according to claim 1, wherein said steps (d)–(f) are repeated automatically.

6. The method according to claim 1, wherein said determining said slice orientation for said at least one magnetic resonance imaging slice in step (f) comprises determining at least two non-parallel slices each containing said contrast material.

7. The method according to claim 6, wherein said determining at least two of said slices comprises determining two orthogonal slices each containing said contrast material.

8. The method according to claim 7, wherein said determining two orthogonal slices comprises determining orthogonal slices aligned along the principal axes of said patient.

9. The method according to claim 1, wherein said step of acquiring said at least one image slice comprises acquiring at least two adjacent and parallel image slices of a portion of said gastrointestinal tract containing said contrast material.

10. The method according to claim 1, wherein said step of acquiring said at least one image slice comprises acquiring at least one thick slice of said portion of said gastrointestinal tract containing said contrast material.

11. The method according to claim 1, wherein said step of acquiring said at least one image slice comprises acquiring at least one initial image slice of a portion of said gastrointestinal tract prior to receiving said contrast material and at least one image slice of said portion of said gastrointestinal tract containing said contrast material, said image slices being substantially coplanar.

12. The method according to claim 11, further comprising the step of subtracting at least a portion of said initial image slice of said portion of said gastrointestinal tract prior to receiving said contrast material from said coplanar image slice of said portion of said gastrointestinal tract containing said contrast material.

13. The method according to claim 1, wherein said step of having said patient ingest said contrast material comprises ingesting a contrast material having a Larmor frequency different from that of hydrogen nuclei within said patient, and wherein said step of acquiring said at least one image slice comprises acquiring said at least one image slice of said portion of said gastrointestinal tract containing said contrast material having said different Larmor frequency.

14. The method according to claim 13, further comprising the step of acquiring at least one additional image slice of said portion at a Larmor frequency different from that of said contrast material, said image slices being substantially coplanar.

15. The method according to claim 14, wherein the step of acquiring said at least one additional image slice comprises acquiring said additional image slice at the Larmor frequency of said hydrogen nuclei within said patient.

16. The method according to claim 14, wherein said steps of acquiring said at least one image slice at the Larmor frequency of said contrast material and of acquiring at least one additional image slice at a different Larmor frequency occur substantially simultaneously.

17. The method according to claim 13, wherein said step of having said patient ingest contrast material having a Larmor frequency different from that of said hydrogen nuclei within said patient comprises ingesting a contrast material having substantially no magnetic resonance imaging signal.

18. The method according to claim 1, wherein said step of calculating the spatial position of said contrast material comprises referencing a look-up table of reference spatial positions of said contrast material passing through said gastrointestinal tract and corresponding passage times of said contrast material therebetween to predict the spatial position of said contrast material within said gastrointestinal tract after the passage of said predetermined period of time.

19. The method according to claim 18, wherein said step of determining a slice orientation comprises referencing a preferred slice orientation from said look-up table corresponding to said spatial position of said contrast material at said predetermined period of time.

20. The method according to claim 18, wherein said step of calculating said spatial position of said contrast material at said predetermined period of time further comprises measuring the actual spatial position of said contrast material within said gastrointestinal tract after said predetermined period of time, computing the difference between said actual spatial position of said contrast material and the predicted spatial position, and computing an adjustment amount for correcting a subsequent predicted spatial position.

21. A method of imaging the dynamic behavior of the gastrointestinal tract of a patient comprising the following steps:

(a) positioning said patient within a magnetic resonance imaging apparatus;

(b) having said patient ingest a magnetic resonance image contrast material;

(c) determining an initial spatial position of said contrast material within the gastrointestinal tract of said patient and an initial orientation for at least one magnetic resonance image of a portion of said gastrointestinal tract containing said contrast material;

(d) acquiring said at least one image;

(e) calculating the spatial position of said contrast material within said gastrointestinal tract of said patient at a predetermined period of time after said acquiring said image;

(f) determining the orientation for at least one magnetic resonance image of another portion of said gastrointestinal tract containing said contrast material at said spatial position; and (g) repeating steps (d)–(f) a plurality of times, each repetition spaced apart for said predetermined period of time, to image the dynamic behavior of at least a portion of said gastrointestinal tract caused by the passage of said contrast material therethrough.

22. The method according to claim 21, wherein said step of acquiring said at least one image comprises acquiring at least one three-dimensional magnetic resonance image of said portion of said gastrointestinal tract containing said contrast material.

23. The method according to claim 21, wherein said step of acquiring said at least one image comprises acquiring at least one image of an esophageal portion of said gastrointestinal tract.

24. The method according to claim 23, wherein said step of acquiring said at least one image comprises acquiring at least one image of said esophageal portion during swallowing.

25. The method according to claim 21, wherein said step of acquiring said at least one image comprises acquiring at least one image of peristaltic action within at least a portion of said gastrointestinal tract caused by said contrast material passing therethrough.

26. The method according to claim 23, wherein said step of acquiring said at least one image comprises acquiring at least one image of a bolus of said contrast material within said gastrointestinal tract.

27. The method according to claim 21, wherein said steps (d)–(f) are repeated a multiplicity of times to create a cine of the dynamic behavior of at least a portion of said gastrointestinal tract of said patient caused by the passage of said contrast material therethrough.

* * * * *